United States Patent [19]
Khoe

[11] Patent Number: 5,466,547
[45] Date of Patent: Nov. 14, 1995

[54] ENTERIC COATED PAPAIN-CONTAINING FOOD SUPPLEMENT FOR CONTROLLING AUTO IMMUNE DISEASES

[76] Inventor: Teng H. Khoe, Marco Polorede 16,, 2725 KR Zoetermeer, Netherlands

[21] Appl. No.: 137,359

[22] Filed: Oct. 18, 1993

[30] Foreign Application Priority Data

Oct. 23, 1992 [NL] Netherlands ............... 9201842

[51] Int. Cl.⁶ ................ A61K 37/54; A61K 47/22
[52] U.S. Cl. ............ 424/439; 424/451; 424/464; 424/490; 424/94.1; 424/94.63; 424/94.66
[58] Field of Search ................... 424/439, 451, 424/464, 490, 94.1, 94.63, 94.66

[56] References Cited

U.S. PATENT DOCUMENTS

| | | | |
|---|---|---|---|
| 4,440,749 | 4/1984 | Fujisaki et al. | 424/94 |
| 4,485,095 | 11/1984 | Fujisaki et al. | 424/94 |
| 5,002,766 | 3/1991 | Ransberger et al. | 424/94.2 |

FOREIGN PATENT DOCUMENTS

| | | |
|---|---|---|
| 0309602 | 4/1989 | European Pat. Off. . |
| 0421022 | 4/1991 | European Pat. Off. . |
| 2848 | 10/1964 | France . |

OTHER PUBLICATIONS

Heinz Sucker et al. "Hilfsstoffe, 3.11 Antioxidanzien", *Pharmazeutische Technologie*, Grorg Thieme Verlag Stuttgart. New York, 1991, pp. 214–216.

J. E. F. Reynolds, *Martindale The Extra Pharmacopoeia*, 29th. ed., London, The Pharmaceutical Press, 1989, p. 1047.

*Primary Examiner*—Nathan M. Nutter
*Attorney, Agent, or Firm*—Henderson & Sturm

[57] ABSTRACT

Food supplement containing enteric coated papain for controlling auto immune diseases, more particularly AIDS and the symptoms of disease related thereto. Vitamin E is added as an antioxidant to papain. Capsules or other oral administration forms are provided with an enteric coating. Papain in the enteric coated form can be administered at a daily dose of 100 mg–5000 mg to a patient having acquired an auto immune disease, more particularly AIDS and the symphtoms of disease related thereto.

13 Claims, 2 Drawing Sheets

ENTERIC COATED PAPAIN-CONTAINING FOOD SUPPLEMENT FOR CONTROLLING AUTO IMMUNE DISEASES

The invention relates to a food supplement for controlling auto immune diseases and symptoms related therewith.

AIDS (acquired immuno deficiency syndrome) is a serious disease which has already affected a large number of people and is rapidly spreading in large parts of the world.

It has hitherto been assumed that AIDS is exclusively caused by HIV virus (human immuno deficiency virus), and all investigations of drugs for the treatment of AIDS in patients with AIDS, in seropositive patients and in ARC patients were based on this assumption.

However, there are indications which suggest that AIDS is not a consequence, or is not exclusively the consequence, of an infection with HIV virus but a consequence of an auto immune disease.

EP-A 0421022 and EP-A 0309602 and U.S. Pat. No. 5,002,766 disclose the use of mixtures of catabolic enzymes, trypsin, α-chymotrypsin, papain, calf thymus, pancreatin and bromelin and mixtures of these enzymes to which pancreatin, bromelin, lipase, amylase and rutin has been added for preparing a pharmaceutical for controlling AIDS.

However, if orally administered papain cannot be active as this enzyme is broken down before entering the small intestine involving the loss of the activity of papain.

Moreover, it is impossible to predict the effect of the other catabolic enzymes on papain after the mixture has been administered.

It has now been found that administration of an enteric coated papain-containing food supplement to subjects suffering from auto immune diseases more particularly AIDS or from conditions connected with AIDS, as well as to seropositive subjects and ARC (AIDS related complex) subjects, leads to a suppression of this condition and to a pronounced improvement in the resistance of such patients.

The invention therefore relates to the use of a food supplement for controlling auto immune diseases, particularly AIDS, and pathological conditions related thereto, wherein the food supplement is an enteric coated papain containing food supplement. Subjects suffering from symptoms connected with AIDS are understood to mean the so-called seropositive and ARC patients.

By using an enteric coated papain containing food supplement, the papain can be administered in a very cheap form and in a simple way as a product to be administered orally.

Although it is at present impossible to provide any experimental proof of the action of papain, it can be assumed that papain, which is a protein-splitting enzyme (protease), is capable of breaking down auto-antibodies in the human body so that drugs which solely act on the HIV virus can never be fully effective. In fact, if it is assumed that AIDS starts as an autoimmune disease, that is to say that auto-antibodies regard their own tissue protein as an exogenous substance to which they are antagonistic, AIDS symptoms should occur even in the absence of HIV virus.

Figure 1:
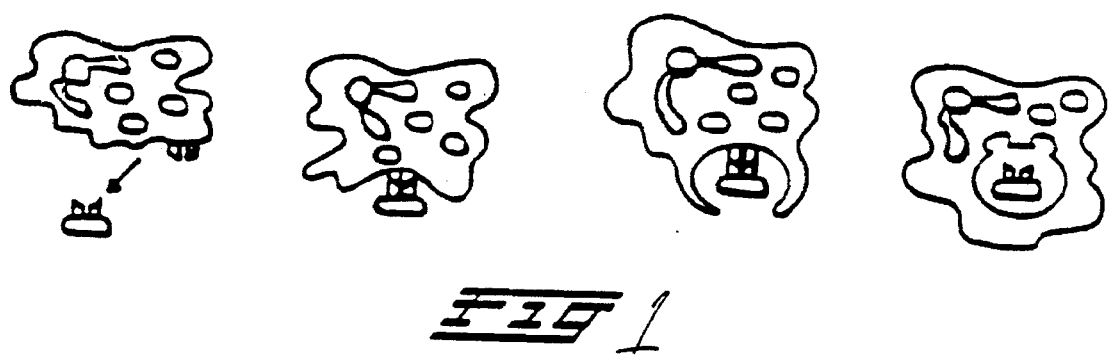
FIG. 1 is an illustration of a model of the human immune defense system based on phagocytosis.
Figure 2:
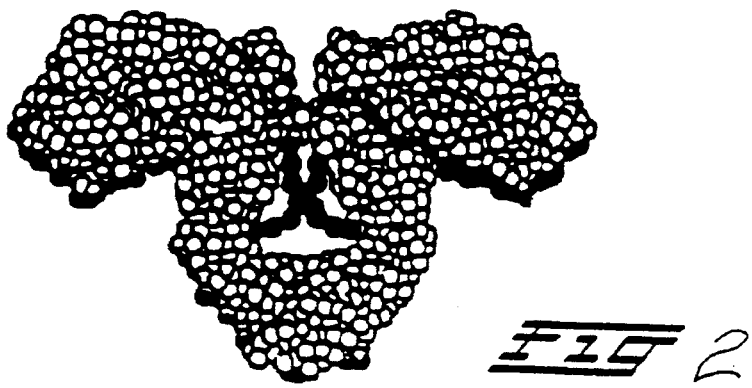
FIG. 2 is an illustration of a computer model of an immunoglobulin acting as an antibody.
Figure 3:
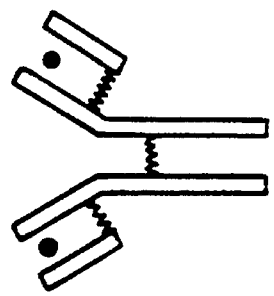
FIG. 3 is a illustration of a simplified model of humoral defense against invading proteins by means of immunoglobulin acting as antibodies.
Figure 4:
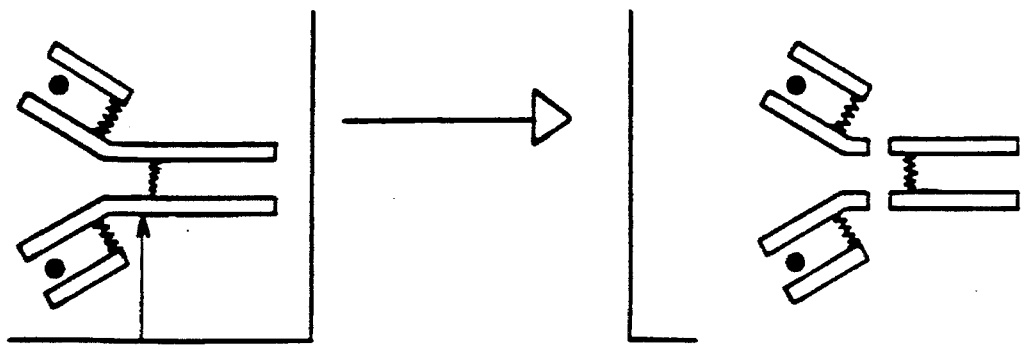
FIG. 4 is a schematic illustration of a reaction between auto antibodies and papain.

It is known from immunology that the resistance of subjects against invading live proteins such as parasites, moulds, bacteria and viruses is based on 2 mechanisms of the immune system, in particular on the following:

1) the cellular defence system based on phagocytosis in which invading proteins adhere to the defensive cells, followed by encapsulation and, finally, destruction of the invaded protein.

A simplified model of this defence can be represented by the appended scheme I.

2) Humoral defence with the aid of immunoglobulins acting as antibodies (diagrammatically illustrated in scheme IV) and complement (a blood-enzyme complex with cascade effect).

A computer model of an immunoglobulin IgG is shown diagrammatically in the appended scheme II and applies both to normal antibodies and to auto-antibodies (AA).

In healthy subjects the two defence systems (1 and 2) interact closely, i.e. when one defence system fails, the other defence system is also switched off and the resistance of the subject drops to virtually zero.

What then are the consequences of, for example, anal passage of sperm in homosexuals, bisexuals and heterosexuals?

The spermatic protein of the donor induces an immunological reaction in the recipient by formation of antibodies. These antibodies against the invading human protein manifest themselves as auto-antibodies against the host protein. In essence, this is a case of cross-sensitivity.

Hypothetically, it would still be possible for an infinite number of variants of antibodies against, for example, 12 of the 18 antigenic determinants of human protein to be produced, especially in view of the numerous contacts of the above-named subjects.

Subsequently, a pathological auto-antibody production process which virtually completely suppresses the physiological production of immunoglobulin starts, so that there is no longer a sufficient defence against other invasions of microorganisms as a result of exhaustion of the humoral defence mechanism.

As a consequence, a patient will go through the seropositive phase and the ARC phase to reach the AIDS stage.

This multi-potential auto-antibody concentration against human protein manifests itself as contagious blood on contact with healthy subjects due to the strongly antigenic properties (development of idiotypes in the partners).

Starting from the above assumption, AIDS must therefore be defined as a severely escalated autoimmune disease.

It will be clear, however, that AIDS symptoms in humans can therefore occur not only on anal passage of sperm. A few other examples are:

a) Contact with blood having a high concentration of antibodies against human protein with multi antigenic diversity on blood transfusion to haemophiliacs.

b) Contact of human blood with contaminated injection needles carrying a high content of antibodies against human protein as contaminant, such as is found in drug addicts.

c) As a result of numerous sexual contacts where the sperm recipient receives the spermatic protein via the anal route. In this case an immunological reaction is generated in the host recipient by formation of antibodies against the recipient's own body protein as a result of which so-called auto-antibodies are formed. These result in an autoimmune disease. These auto-antibodies use up the available defensive immunoglobulins of the host (generally of the IgG class), so that no resistance can be offered to other infections and the AIDS phase is therefore quickly reached.

d) As a result of starvation, when a person is no longer able to take in proteins which are necessary for the production of defensive immunoglobulins which protect precisely against invasion of infectious microorganisms. This state is encountered in various African and Asian countries.

Thus, in theory, AIDS can occur spontaneously without any initial HIV infection, caused by, for example, inappropriate sexual behaviour (see item c above) or violation of the laws of nature of the immune system in addition to by nature frequently changing contacts.

Administration of enteric coated papain, which is a protein-splitting enzyme, to such subjects with AIDS symptoms leads to the following mechanism: Lymphocyte→auto-antibody+papain→2×F (ab)+ 1×F (c)

This reaction is explained in greater detail in the appended reaction scheme III from which it is evident that an auto-antibody (AA) which can bind to an endogenous antigen (A) is broken down into three inactive parts on exposure to papain. These inactive parts are F(ab), or F (Fraction antigen binding) and F (Fraction constant).

For the treatment of AIDS symptoms it is advisable to administer to the patient about 300 mg to about 5000 mg enteric coated papain a day, divided over a maximum of 12 doses which are administered, for example, at hourly intervals by the oral route, for a single 7-day period or for two 7-day periods. The 7-day period is based on the mean lifetime of a beta-lymphocyte, which beta-lymphocytes, as the production cells of immunoglobulins, under pathological circumstances produce mainly auto-antibodies as well as small amounts of normal immunoglobulin for the defence, as a result of which microorganisms can easily enter the body. After stepwise increases of the dose, the final dose for an adult having a body weight of 60 kg is adjusted to, for example, nine times 1 capsule containing 100 mg papain a day, administered every 1½ hours, or more.

At the end of the above-mentioned period there is a period of rest before a new course of treatment lasting 1 or 2 weeks is repeated.

If more than 900 mg a day are administered there is the possibility of intestinal erosions on obstruction or cumulation.

In order to prevent oxidation of papain, vitamin E is added as a non-toxic antioxidant.

In order to prevent breakdown of papain on oral administration, the forms which can be administered orally, such as capsules, are provided with an enteric coating.

Although papain itself breaks down normal, good antibodies as well as auto-antibodies, papain can render the auto-antibodies virtually inactive because the fractions are easily passed via the urine.

This is due to the fact that newly formed β-lymphocytes having a lifetime of 7 days themselves always produce good antibodies but on contact with strange human antigenic determinants switch to the production of new auto-antibodies.

Since every administration of papain leads to breakdown of auto-antibodies and the risk of newly formed β-lymphocytes meeting strange human antigens is minimalized, the lymphocytes will form virtually no auto-antibodies after some time.

When a total of 50% auto-antibodies and 50% normal antibodies is present, papain will break down, for example, half of all the antibodies including both auto-antibodies and normal antibodies.

After this initial treatment, the β-lymphocytes will again replenish the antibodies. However, since only 25% auto-antibodies are present, less than 25% of the newly formed β-lymphocytes with less provocation will start to form auto-antibodies, while the remainder will form normal antibodies. This means that more than 50% normal antibodies are formed and less than 50% auto-antibodies. On several treatments with papain, an increasing number of normal antibodies will appear in the blood, so that AIDS symptoms will not longer occur.

Assuming, for example, a mean blood volume of 5000 ml and 80 g healthy standard immunoglobulins in an adult weighing 60 kg, if, hypothetically all these immunoglobulins are transformed into auto-antibodies due to antigen provocation, 2.5 g papain are sufficient for breaking down 80 g of auto-antibodies (AA), i.e. 1 g papain per 35 g auto-antibodies (AA). If the administration of papain lasts at least as long as the lifetime of an average beta-lymphocyte (7 days, or a multiple thereof), a new generation of beta-lymphocytes is formed which produce healthy, normal immunoglobulins because of their DNA structure, so that again sufficient resistance is developed against infections.

It is advisable to start the papain treatment in the seropositive phase of a patient in order to extend the incubation period up to the ARC phase for as long as possible and to keep the patient alive in a normal manner.

It is to be noted that the above-mentioned assumptions do not limit the protection applied for in any way.

The food supplement according to the invention is also suitable for controlling auto immune diseases such as e.g. Multiple sclerosis, Mobus Crohn, Sarcoidose, Colitis ulcerosa and S.E.L. disease.

The invention will now be illustrated by means of a few exemplary embodiments.

EXAMPLE 1

Capsules with an enteric coating and containing 65 mg papain and vitamin E are prepared as a food supplement.

These capsules are administered to an adult seropositive patient of 40 years of age with a body weight of 60 kg. Oral administration comprises 3 capsules 5 times a day every 3 hours which are to be taken with a little bread and water, equivalent to 975 mg papain a day.

The treatment comprises a first course of treatment with administration of the above capsules for 5 days followed by 1 day of rest and another 5 days of administration of the medicament.

After 1 week of rest, where necessary, administration is reduced to 3 capsules twice a day for 32 days, also referred to as the second course of treatment.

If symptoms recur the first course of treatment is repeated.

It must be mentioned in this connection that T-lymphocytes from the thymus can remain dormant in blood for many years and become active again, i.e. can produce auto-antibodies again, but only if they have done so in an earlier stage.

EXAMPLE 2

Capsules with an enteric coating and containing 100 mg papain and vitamin E are prepared.

The capsules are administered to a seropositive patient of 40 years of age having a body weight of 60 kg.

Two capsules are administered orally 5 times a day every 3 hours with a little bread and water, equivalent to 1000 mg papain a day.

After administration for 5 days there is 1 day of rest followed by another 5 days of administration of the above-mentioned capsules (this administration is called the first course of treatment).

After 1 week of rest, where necessary, the number of capsules administered is reduced to 2 capsules twice a day for 32 days, and this administration is called the second course of treatment.

If symptoms recur the second course of treatment is repeated.

Thymus lymphocytes (T-lymphocytes) which previously produced auto-antibodies can be activated again after many years of dormancy, and in this case it is advisable to repeat the first and/or second course of treatment.

EXAMPLE 3

Capsules having an enteric coating and containing 65 mg papain and vitamin E are prepared.

These capsules are taken orally six times a day in a dose of 3 capsules every 2 hours with a little bread and a little water, so that 1170 mg papain is administered each day to the patient with ARC status. The body weight of the patient is 60 kg and he is 40 years old.

After daily administration as described above for 5 days, treatment is interrupted for one day, and then the above-mentioned number of capsules is administered again for another 4 days. This represents the first course of treatment.

After an interruption of 1 week, the number of capsules administered is reduced to 3 capsules twice a day for 32 days. This treatment represents the second course of treatment.

If the initial symptoms of AIDS recur the first course of treatment and/or the second course of treatment are/is repeated.

EXAMPLE 4

Capsules having an enteric coating and containing 100 mg papain and vitamin E are prepared, and these are administered to a patient with ARC symptoms who is 40 years of age and has a body weight of 60 kg.

The capsules mentioned above are taken orally six times a day in a dose of 2 capsules every 2 hours with a little bread and water, equivalent to 1200 mg papain a day.

After administration of the above-described number of capsules for 5 days, treatment is interrupted for 1 day, and thereafter the above-mentioned treatment is continued for another 4 days. This represents the first course of treatment.

After a 1-week interruption of administration the dose is reduced to 2 capsules twice a day for 32 days. This represents the second course of treatment. If symptoms recur the first or second course of treatment is repeated.

EXAMPLE 5

Capsules having an enteric coating and containing 100 mg papain and vitamin E are prepared, and these are administered to an adult patient 40 years of age and having a body weight of 60 kg, who clearly has AIDS status.

Two capsules are taken orally every two hours six times a day with a little bread and water, so that 1200 mg papain are administered orally each day.

After 5 days of this oral administration, treatment is stopped for 1 day, and after this the above-described numbers of capsules are administered for another 4 days. This represents the first course of treatment.

The amount of orally administered papain is then reduced to 2 capsules twice a day for 32 days. This represents the second course of treatment.

In the case of recurrence of symptoms of the disease as a result of memory cells, the first and/or the second course of treatment are/is repeated.

EXAMPLE 6

Example 1 is repeated for a patient suffering from Multiple sclerosis, Mobus Crohn, Sarcoidose, Colitis ulcerosa and S.L.E. (systemic lupus erythematosus) disease respectively.

The results are the same as for a patient suffering from AIDS as in Example 1.

What is claimed is:

1. A food supplement for controlling auto immune disease, said food supplement comprising an enteric composition comprising papain and Vitamin E, said papain being present in an effective amount for administering to a patient having an auto immune disease.

2. The food supplement according to claim 1, wherein said papain comprises Carico papaya.

3. The food supplement according to claim 1, wherein said composition comprises a form suitable for oral administration.

4. The food supplement according to claim 1, wherein said form suitable for oral administration comprises an enteric capsule comprising an effective amount of papain within a range of about 50 to 100 mg papain.

5. The food supplement according to claim 1, wherein said effective amount of papain comprises a daily dose amount within a range of about 100 to 5000 mg.

6. A method for controlling auto immune disease, said method comprising administering a food supplement comprising an enteric composition comprising papain and Vitamin E, said papain being present in an effective amount for administering to a patient having an auto immune disease, to a patient having an auto immune disease.

7. A method for treating auto immune disease, said method comprising administering a food supplement comprising an enteric composition comprising papain and Vitamin E, said papain being present in an effective amount for administering to a patient having an auto immune disease.

8. The method according to claim 2, wherein said papain comprises Carico papaya.

9. The method according to claim 2, wherein said composition comprises a form suitable for oral administration.

10. The method according to claim 2, wherein said form suitable for oral administration comprises an enteric capsule comprising an effective amount of papain within a range of about 50 to 100 mg papain.

11. The method according to claim 2, wherein said effective amount of papain comprises a daily dose amount within a range of about 100 to 5000 mg.

12. The method according to claim 6, wherein said auto immune disease comprises acquired immuno deficiency syndrome.

13. The method according to claim 7, wherein said auto immune disease comprises acquired immuno deficiency syndrome.

* * * * *